(12) United States Patent
Anstadt

(10) Patent No.: US 12,741,134 B2
(45) Date of Patent: Sep. 22, 2026

(54) SINGLE TUBE PRESSURIZATION SYSTEM FOR A HEART PUMP

(71) Applicant: Lifebridge Technologies LLC, Dayton, OH (US)

(72) Inventor: Mark P. Anstadt, Kettering, OH (US)

(73) Assignee: Lifebridge Technologies LLC, Dayton, OH (US)

( * ) Notice: Subject to any disclaimer, the term of this patent is extended or adjusted under 35 U.S.C. 154(b) by 0 days.

(21) Appl. No.: 19/352,364

(22) Filed: Oct. 7, 2025

(65) Prior Publication Data

US 2026/0033950 A1 Feb. 5, 2026

Related U.S. Application Data

(60) Division of application No. 18/393,661, filed on Dec. 21, 2023, now Pat. No. 12,478,475, which is a (Continued)

(51) Int. Cl.
*A61M 60/191* (2021.01)
*A61F 2/24* (2006.01)
(Continued)

(52) U.S. Cl.
CPC ......... *A61M 60/191* (2021.01); *A61F 2/2481* (2013.01); *A61M 60/289* (2021.01); (Continued)

(58) Field of Classification Search
CPC ............ A61F 2/2481; A61F 2250/0058; A61F 2250/0003; A61M 60/289; A61M 60/191; (Continued)

(56) References Cited

U.S. PATENT DOCUMENTS 2,826,193 A 3/1958 Vineberg
2,889,780 A 6/1959 Binford
(Continued)

FOREIGN PATENT DOCUMENTS

JP 2002-532189 10/2002
JP 2007-524464 10/2007
(Continued)

OTHER PUBLICATIONS

Song, Ruoyu et al. (2019). Causes of Desktop FDM Fabrication Failures in an Open Studio Environment. Procedia CIRP. 80. 494-499. (Year: 2019).

(Continued)

*Primary Examiner* — Pamela M. Bays
(74) *Attorney, Agent, or Firm* — LaMorte & Associates PC

(57) ABSTRACT

A fluid controlled system for a cardiac assist device and its method of operation. The cardiac assist device has a cup assembly with a receptacle area. The cup assembly has at least one inflatable membrane that expands into the receptacle area. A single pressure tube connects the cup assembly to a fluid pump. A valve assembly is incorporated into the cardiac assist device. The valve assembly includes at least one valve that controls fluid flow between the inflatable membranes and the pressure tube and/or fluid flow between the receptacle area and the pressure tube. The valve assembly controls fluid flow to advance the cup assembly onto the heart, to maintain the cup assembly in an operable position, to operate the cup assembly, and to remove the cup assembly.

11 Claims, 13 Drawing Sheets

Related U.S. Application Data continuation-in-part of application No. 18/509,260, filed on Nov. 14, 2023, now Pat. No. 12,616,827, which is a continuation-in-part of application No. 18/447,786, filed on Aug. 10, 2023, now Pat. No. 12,115,363, and a continuation-in-part of application No. 18/160,963, filed on Jan. 27, 2023, now Pat. No. 11,896,812, and a continuation-in-part of application No. 18/150,746, filed on Jan. 5, 2023, now Pat. No. 12,263,332, which is a continuation-in-part of application No. 17/931,853, filed on Sep. 13, 2022, now abandoned, said application No. 18/509,260 is a continuation-in-part of application No. 17/825,343, filed on May 26, 2022, which is a continuation-in-part of application No. 17/208,776, filed on Mar. 22, 2021, now Pat. No. 11,383,076.

(60) Provisional application No. 63/086,478, filed on Oct. 1, 2020.

(51) Int. Cl.
*A61M 60/289* (2021.01)
*A61M 60/468* (2021.01)
*A61M 60/435* (2021.01)
*A61M 60/515* (2021.01)

(52) U.S. Cl.
CPC ... *A61M 60/468* (2021.01); *A61F 2250/0003* (2013.01); *A61F 2250/0058* (2013.01); *A61M 60/435* (2021.01); *A61M 60/515* (2021.01)

(58) Field of Classification Search
CPC . A61M 60/468; A61M 60/515; A61M 60/435
See application file for complete search history.

(56) References Cited

U.S. PATENT DOCUMENTS 3,053,249 A * 9/1962 Smith ................ A61M 60/191 601/153
3,233,607 A 2/1966 Bolie
3,279,464 A 10/1966 Kline
3,304,501 A 2/1967 Ruthenberg
3,371,662 A 3/1968 Heid
3,376,863 A 4/1968 Kolobow
3,449,767 A 6/1969 Bolie
3,455,298 A 7/1969 Anstadt
3,478,737 A 11/1969 Rassman
3,513,836 A 5/1970 Sausse
3,587,567 A 6/1971 Schiff
3,590,815 A 7/1971 Schiff
3,613,672 A 10/1971 Schiff
3,674,381 A 7/1972 Schiff
4,048,990 A 9/1977 Goetz
4,192,293 A 3/1980 Asrican
4,281,669 A 8/1981 MacGregor
4,448,190 A 5/1984 Freeman
4,536,893 A 8/1985 Parravicini
4,609,176 A 9/1986 Powers
4,621,617 A 11/1986 Sharma
4,662,358 A 5/1987 Farrar
4,684,143 A 8/1987 Sato
4,957,477 A 9/1990 Lundback
4,979,936 A 12/1990 Stephenson
5,066,111 A 11/1991 Inokuchi
5,089,017 A 2/1992 Young
5,098,369 A 3/1992 Heilman et al.
5,098,442 A 3/1992 Grandjean
5,119,804 A 6/1992 Anstadt
5,131,905 A 7/1992 Grooters
5,156,154 A 10/1992 Valenta, Jr. et al.
5,158,978 A 10/1992 Rubin
5,169,381 A 12/1992 Snyders
5,199,804 A 4/1993 Rimbey et al.
5,205,722 A 4/1993 Hammond
5,256,132 A 10/1993 Snyders
5,273,518 A 12/1993 Lee et al.
5,322,067 A 6/1994 Prater
5,330,505 A 7/1994 Cohen
5,364,337 A 11/1994 Guiraudon et al.
5,368,451 A 11/1994 Hammond
5,374,287 A 12/1994 Rubin
5,383,840 A 1/1995 Heilman et al.
5,385,528 A 1/1995 Wilk
5,429,584 A 7/1995 Chiu
5,476,502 A 12/1995 Rubin
5,496,353 A 3/1996 Grandjean et al.
5,533,958 A 7/1996 Wilk
5,558,617 A 9/1996 Heilman et al.
5,562,595 A 10/1996 Neisz
5,658,237 A 8/1997 Francischelli
5,674,259 A 10/1997 Gray
5,697,884 A 12/1997 Francischelli et al.
5,697,952 A 12/1997 Francischelli et al.
5,707,336 A 1/1998 Rubin
5,713,954 A 2/1998 Rosenberg et al.
5,716,379 A 2/1998 Bourgeois et al.
5,738,627 A 4/1998 Kovacs et al.
5,749,839 A 5/1998 Kovacs
5,769,800 A 6/1998 Gelfand et al.
5,800,334 A 9/1998 Wilk
5,861,558 A 1/1999 Buhl et al.
5,876,345 A 3/1999 Eaton et al.
5,902,229 A 5/1999 Tsitlik et al.
5,908,378 A 6/1999 Kovacs et al.
5,910,124 A 6/1999 Rubin
5,919,209 A 7/1999 Schouten
5,971,910 A 10/1999 Tsitlik et al.
5,971,911 A 10/1999 Wilk
5,980,571 A 11/1999 Nomura et al.
6,042,532 A 3/2000 Freed et al.
6,044,298 A 3/2000 Salo et al.
6,059,750 A 5/2000 Fogarty et al.
6,076,013 A 6/2000 Brennan et al.
6,095,968 A 8/2000 Snyders
6,110,098 A 8/2000 Renirie et al.
6,123,726 A 9/2000 Mori et al.
6,132,363 A 10/2000 Freed et al.
6,183,412 B1 2/2001 Benkowski et al.
6,206,820 B1 3/2001 Kazi et al.
6,224,540 B1 5/2001 Lederman et al.
6,238,334 B1 5/2001 Easterbrook, III et al.
6,251,061 B1 6/2001 Hastings et al.
6,254,525 B1 7/2001 Reinhardt et al.
6,282,445 B1 8/2001 Reinhardt et al.
6,298,266 B1 10/2001 Rubin et al.
6,309,380 B1 10/2001 Larson et al.
6,328,689 B1 12/2001 Gonzalez et al.
6,408,205 B1 6/2002 Renirie et al.
6,432,039 B1 8/2002 Wardle
6,438,411 B1 8/2002 Guttman et al.
6,464,655 B1 10/2002 Shahinpoor
6,485,407 B2 11/2002 Alferness et al.
6,508,756 B1 1/2003 Kung et al.
6,540,659 B1 4/2003 Milbocker
6,547,716 B1 4/2003 Milbocker
6,572,534 B1 6/2003 Milbocker et al.
6,602,182 B1 8/2003 Milbocker
6,612,978 B2 9/2003 Lau et al.
6,616,596 B1 9/2003 Milbocker
6,622,045 B2 9/2003 Snell et al.
6,626,821 B1 9/2003 Kung et al.
6,641,604 B1 11/2003 Adelman et al.
6,682,474 B2 1/2004 Lau et al.
6,730,016 B1 5/2004 Cox et al.
6,757,561 B2 6/2004 Rubin et al.
6,808,483 B1 10/2004 Ortiz et al.
6,846,296 B1 1/2005 Milbocker et al.
6,971,127 B2 12/2005 Richards
7,331,221 B2 2/2008 Wise et al.
7,494,459 B2 2/2009 Anstadt et al.
7,871,366 B2 1/2011 Criscione et al.

(56) References Cited

U.S. PATENT DOCUMENTS 8,187,160 B2 5/2012 Criscione et al.
8,460,181 B2 6/2013 Saadat et al.
10,058,647 B2 8/2018 Roche et al.
10,463,496 B2 11/2019 Criscione et al.
11,191,944 B2 12/2021 Tuval et al.
11,511,102 B2 11/2022 Criscione et al.
11,752,321 B2 9/2023 Pilla et al.
12,115,363 B1 10/2024 Anstadt
12,161,857 B2 12/2024 Saul et al.
12,226,622 B2 2/2025 Kheradvar et al.
2001/0002445 A1* 5/2001 Vesely .................. A61F 2/2439 623/2.11
2001/0041821 A1 11/2001 Wilk
2002/0173693 A1 11/2002 Landesberg
2003/0032855 A1 2/2003 Shahinpoor
2004/0010180 A1 1/2004 Scorvo
2004/0024315 A1 2/2004 Chalana
2004/0059183 A1 3/2004 Jozef et al.
2004/0078067 A1 4/2004 Thompson et al.
2004/0102674 A1 5/2004 Zadini et al.
2004/0116769 A1 6/2004 Jassawalla
2004/0167375 A1 8/2004 Couvillon
2004/0225177 A1 11/2004 Coleman et al.
2004/0267086 A1 12/2004 Anstadt et al.
2005/0113632 A1 5/2005 Ortiz et al.
2005/0148814 A1 7/2005 Fischi et al.
2005/0234289 A1 10/2005 Anstadt et al.
2006/0106442 A1 5/2006 Richardson
2006/0129025 A1 6/2006 Levine et al.
2006/0142634 A1 6/2006 Anstadt et al.
2006/0167334 A1 7/2006 Anstadt et al.
2006/0211909 A1 9/2006 Anstadt et al.
2007/0197859 A1 8/2007 Schaer et al.
2008/0081944 A1 4/2008 Lau et al.
2008/0255629 A1 10/2008 Jenson
2008/0257412 A1 10/2008 Gordon
2009/0036730 A1 2/2009 Criscione et al.
2009/0099498 A1 4/2009 Demers et al.
2010/0081867 A1 4/2010 Fishler
2010/0152523 A1 6/2010 MacDonald et al.
2010/0191071 A1 7/2010 Anderson
2011/0196189 A1 8/2011 Milbocker
2011/0288367 A1 11/2011 Miller
2012/0095498 A1 4/2012 Stefanchik et al.
2013/0102849 A1 4/2013 Criscione
2015/0018607 A1 1/2015 Akita
2015/0080640 A1 3/2015 Lillehei
2016/0101230 A1 4/2016 Ochsner
2016/0151552 A1 6/2016 Solem
2016/0262889 A1 9/2016 Laham
2016/0262890 A1 9/2016 Hjelle et al.
2016/0346449 A1 12/2016 Roche
2017/0258593 A1 9/2017 Good et al.
2018/0153709 A1 6/2018 Hunter
2019/0209759 A1 7/2019 Vasilyev et al.
2019/0224395 A1 7/2019 Pilla et al.
2020/0085579 A1 3/2020 Kim
2022/0013211 A1 1/2022 Steinberg
2022/0249830 A1 8/2022 Kanz
2023/0060284 A1 3/2023 Siess et al.
2023/0071248 A1 3/2023 Keenan et al.
2024/0082566 A1 3/2024 Anstadt
2024/0099846 A1 3/2024 Anstadt
2024/0216652 A1 7/2024 Keenan et al.
2024/0269459 A1 8/2024 Schellenberg et al.

FOREIGN PATENT DOCUMENTS

WO WO 00/78375 12/2000
WO WO2005/091860 10/2005
WO WO2006/122036 11/2006
WO WO2008/127607 10/2008

OTHER PUBLICATIONS

Devore. "24-segment sphericity index: a new technique to evaluate fetal cardiac diastolic shape" 650-658. Ultrasound in obstetrics & gynecology. Https://pubmed.ncbi.nlm.nih.gov/284_37575/, May 2018; <DOI:10.1002/uog. 17505>.

* cited by examiner

PRESSURE PROFILE
TO/FROM PNEUMATIC PUMP

PRESSURE > P2

PRESSURE PROFILE
TO/FROM PNEUMATIC PUMP

P3 < PRESSURE< P1

PRESSURE PROFILE
TO/FROM PNEUMATIC PUMP

*PRESSURE > P2*

SINGLE TUBE PRESSURIZATION SYSTEM FOR A HEART PUMP

RELATED APPLICATIONS

This application is a continuation-in-part of co-pending U.S. application Ser. No. 18/509,260 filed Nov. 14, 2023.

BACKGROUND OF THE INVENTION

1. Field Of The Invention

In general, the present invention relates to heart pumps that contain inflatable membranes that are selectively inflated using variable air or liquid fluid pressures. More particularly, the present invention relates to the structure of the heart pump and the features that regulate the flow of fluid pressure within the structure of the heart pump.

2. Prior Art Description

There are many instances when a heart needs assistance to maintain a proper blood flow in a patient. Often hearts that are diseased, failing, or have stopped need the application of a cardiac assist system to prevent a patient from dying. Additionally, the proper mechanical massaging of the failing heart may have additional therapeutic implications for recovery. In the prior art, there are many constructs that surround the ventricles of the heart and apply external forces to the ventricles. The heart is a complex organ that both empties and fills as it pumps. In order for a heart to pump blood effectively and efficiently, a heart often needs assistance in both filling and emptying. Such assistance is typically supplied to the heart by placing a cup-shaped heart pump over the ventricles of the heart.

In the prior art, there are several cup-shaped heart pumps that fit over the ventricles of the heart. Such prior art heart pumps are exemplified by U.S. Pat. No. 3,455,298, to Dr. George Anstadt. This heart pump has a stiff outer shell and an inflatable inner membrane. The outer shell and inflatable membrane are placed around the ventricles of the heart. When the inflatable membrane expands, the inflatable membrane compresses the heart, therein helping with the heart's emptying, or its systolic, function when native heart function is still present. When the membrane deflates, there is a negative pressure that is created between the tissue of the heart and the stiff outer shell. This negative pressure assists the heart in filling, or with its diastolic pump function, when native heart function is still present.

In U.S. patent application Ser. No. 18/150,746, filed Jan. 5, 2023, a heart pump is described that has multiple inflatable membranes and a flexible outer shell. The controlled inflation of the inflatable membranes and the flexing of the outer shell are customized to provide specific forces that meet the needs of a particular heart.

If a cup-shaped heart pump is utilized that contains one or more inflatable membranes, varying positive fluid pressures must be supplied to control the forces being applied to the heart by the inflatable membranes. Furthermore, in order for the cup-shaped heart pump to pass over the ventricles of the heart, suction must also be supplied. The suction helps pull the cup-shaped heart pump onto the heart during insertion and maintains the heart pump in position when the heart pump is activated. The suction also facilitates adherence of the heart pump's membrane to the heart's surface during the phase of diastolic pump function augmentation and/or augmenting filling of the ventricles by the device. Since both negative fluid forces, i.e., suction, and positive fluid forces are required at the same time, different tubes are provided. Typically, a suction tube is provided at the apex of the cup structure and separate pressure tubes are provided for each of the inflatable membranes. However the suction tube can be extended to other sites particularly with regards to minimally invasive insertion as the suction can provide a leading edge of vacuum for the device in this constructs. The suction tube maintains a negative pressure between the heart and the cup-structure of the pump. The pressure tubes supply variable positive pressure to the inflatable membranes.

The cup-shaped heart pump is advanced into the body through an incision. If a minimally invasive surgical procedure is being conducted, the incision can be small. The same incision is also used by the surgeon to advance and manipulate instruments. Accordingly, the presence of multiple tubes passing through the incisions are problematic. The presence of the tubes reduce the usable space available to the surgeon. Furthermore, since the tubes experience changing internal pressures, the tubes flex and move during the operation. This movement can adversely affect the other instruments being used by the surgeon.

A need therefore exists for an improved system for operating a heart pump that uses only one tube to provide both positive and negative fluid pressures to the heart pump. A single tube takes up much less space than multiple tubes. Furthermore, a single tube is easier to limit in its motions during an operation. This need is met by the present invention as described and claimed below.

SUMMARY OF THE INVENTION

The present invention is a fluid control system for a cardiac assist device and its associated method of operation. The cardiac assist device has a cup assembly that defines a receptacle area. The receptacle area receives a portion of a patient's heart therein. The cup assembly has at least one inflatable membrane that selectively expands into the receptacle area when inflated.

A single pressure tube connects the cup assembly to a fluid pump. The fluid pump alters the gas or liquid fluid flow to and from the cup assembly in accordance with a programmed pressure profile.

A valve assembly is incorporated into the cardiac assist device. The valve assembly includes one or more valves. A pressure valve controls fluid flow between the receptacle area and the single pressure tube. An optional control valve controls fluid flow between the inflatable membranes and the single pressure tube.

By providing a valve assembly that is responsive to different pressures, fluid flow from the single pressure tube can be used to advance the cup assembly onto the heart, to maintain the cup assembly in an operable position, to operate the cup assembly, and to remove the cup assembly from the heart. The use of a single pressure tube makes the overall system highly useful for minimally invasive surgical procedures.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention system and methodology can be embodied in many ways, only some exemplary embodiments are illustrated and described. The exemplary embodiments are being shown for the purposes of explanation and description. The exemplary embodiments are selected in order to set forth some of the best modes contemplated for the invention. The illustrated embodiments, however, are merely exemplary and should not be considered as limitations when interpreting the scope of the appended claims.

Figure 1:
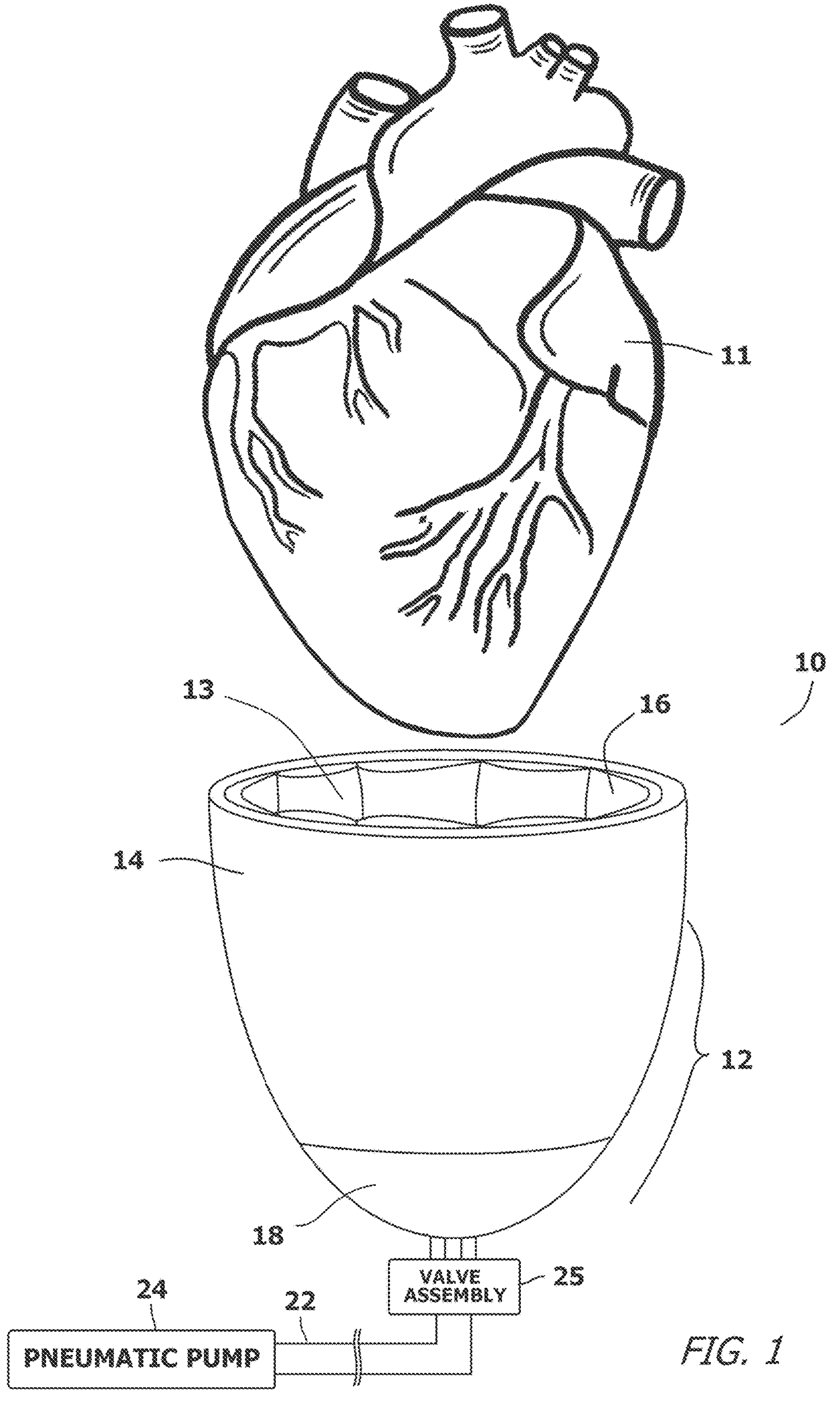
FIG. 1 shows an exemplary embodiment of a cardiac assist system shown in conjunction with a heart.
Figure 2:
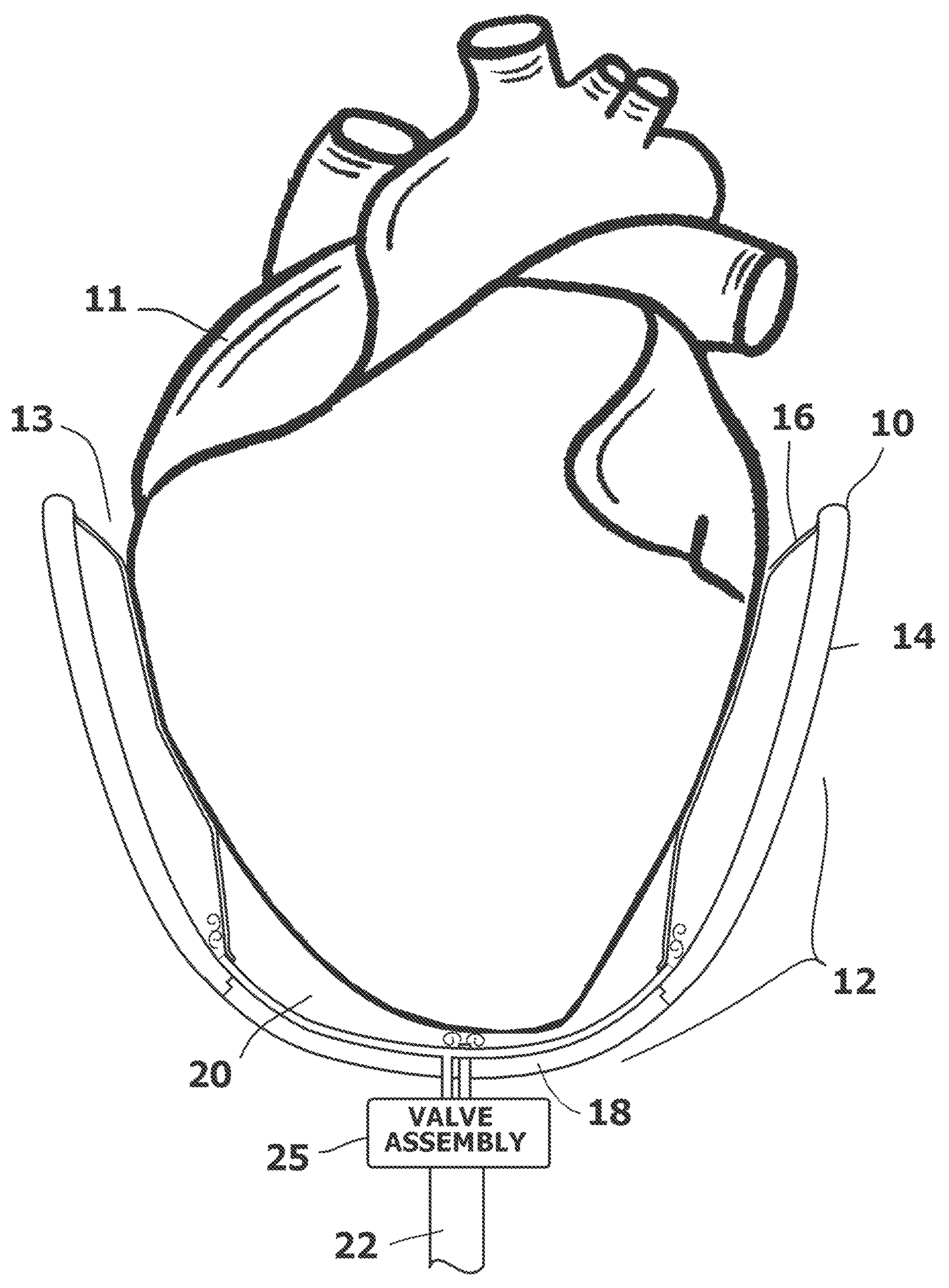
FIG. 2 shows a cross-section of the embodiment of FIG. 1 with the cardiac assist system engaging the heart.

Referring to FIG. 1 and FIG. 2, a cardiac assist system 10 is shown in conjunction with a heart 11. The cardiac assist system 10 contains a cup assembly 12. The cup assembly 12 defines a receptacle area 13 that can receive at least some portion of the heart 11. The cup assembly 12 includes an outer shell 14 that is internally lined with one or more inflatable membranes 16. The outer shell 14 is set upon an apical endcap 18 to complete the cup assembly 12.

When the cup assembly 12 is advanced over the heart 11, there is an interface gap 20 between the apical endcap 18 of the cup assembly 12 and the ventricles of the heart 11. This interface gap 20 must be maintained at negative pressure, relative to ambient air pressure, in order to maintain good position and contact between the cup assembly 12 and the heart 11 in the receptacle area 13. Furthermore, the inflatable membranes 16 must be inflated at a positive pressure, relative to ambient air pressure, in order to apply forces to the heart 11. Both the positive and negative fluid pressures are supplied through a single primary tube 22. The primary tube 22 extends from the cup assembly 12 to a programable fluid pump 24. The programable fluid pump can pump either a gas, such as air, or a liquid, such as saline. The programable fluid pump 24 can provide positive and negative fluid pressures at different times in accordance with a programmed pressure profile that is used to operate the cardiac assist system 10. The pressure profile created by the programable fluid pump 25 is communicated to the inflatable membranes 16 and the interface gap 20 through a specialized valve assembly 25.

Figure 3:
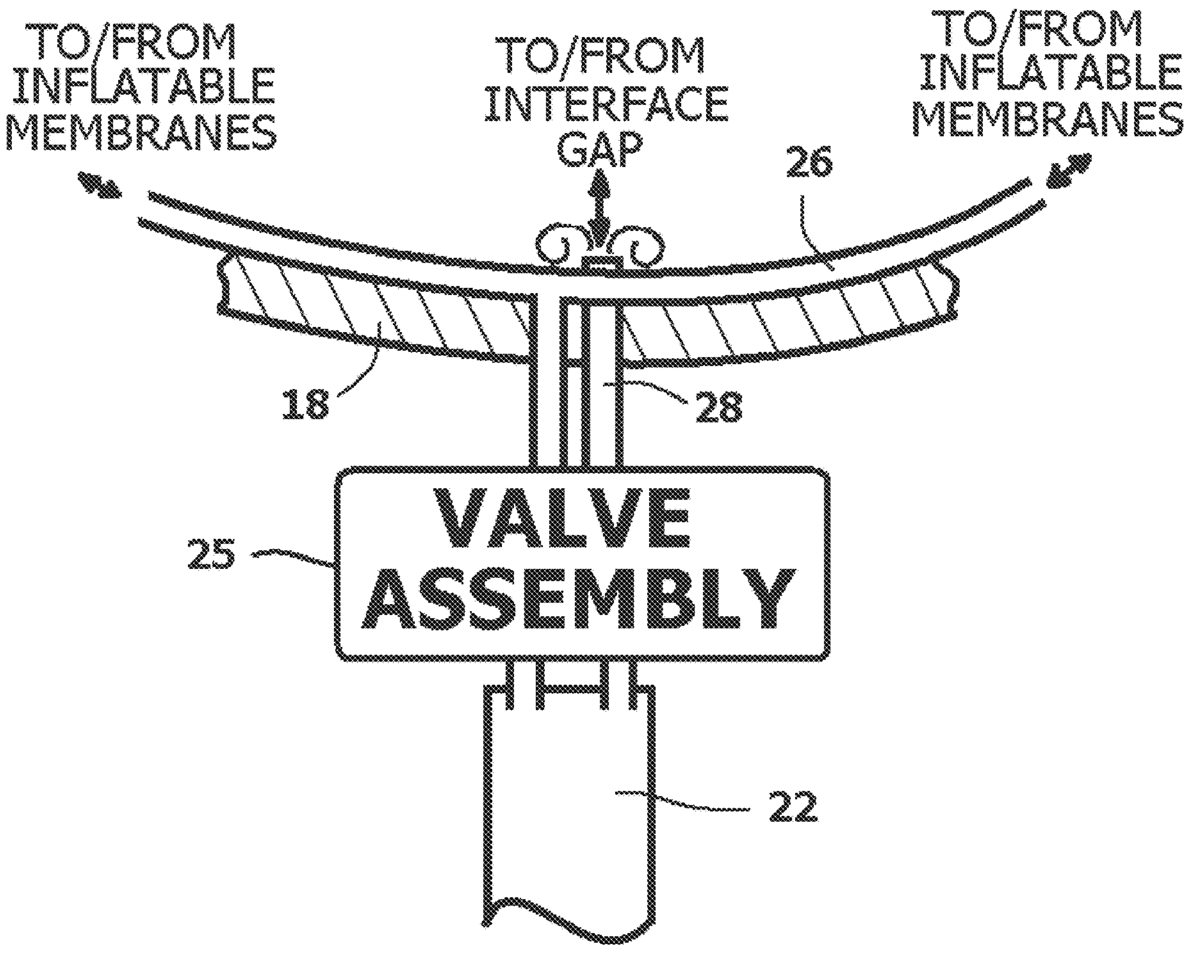
FIG. 3 is an enlarged view of a portion of FIG. 2 to emphasize the fluid flow features.

Referring to FIG. 3 in conjunction with FIG. 2, it can be seen that at least one conduit or secondary tube 26 leads from each individual inflatable membrane 16 toward the primary tube 22. The secondary tubes 26 are used to selectively inflate the inflatable membranes 16. Likewise, at least one conduit or tertiary tube 28 extends through the apical endcap 18 toward the primary tube 22. The tertiary tube 28 is used to provide suction to the interface gap 20 between the apical endcap 18 of the cup assembly 12 and the ventricles of the heart 11. The fluid flow between the primary tube 22 and both the secondary tubes 26 and the tertiary tube 28 are controlled by a valve assembly 25.

Figure 4:
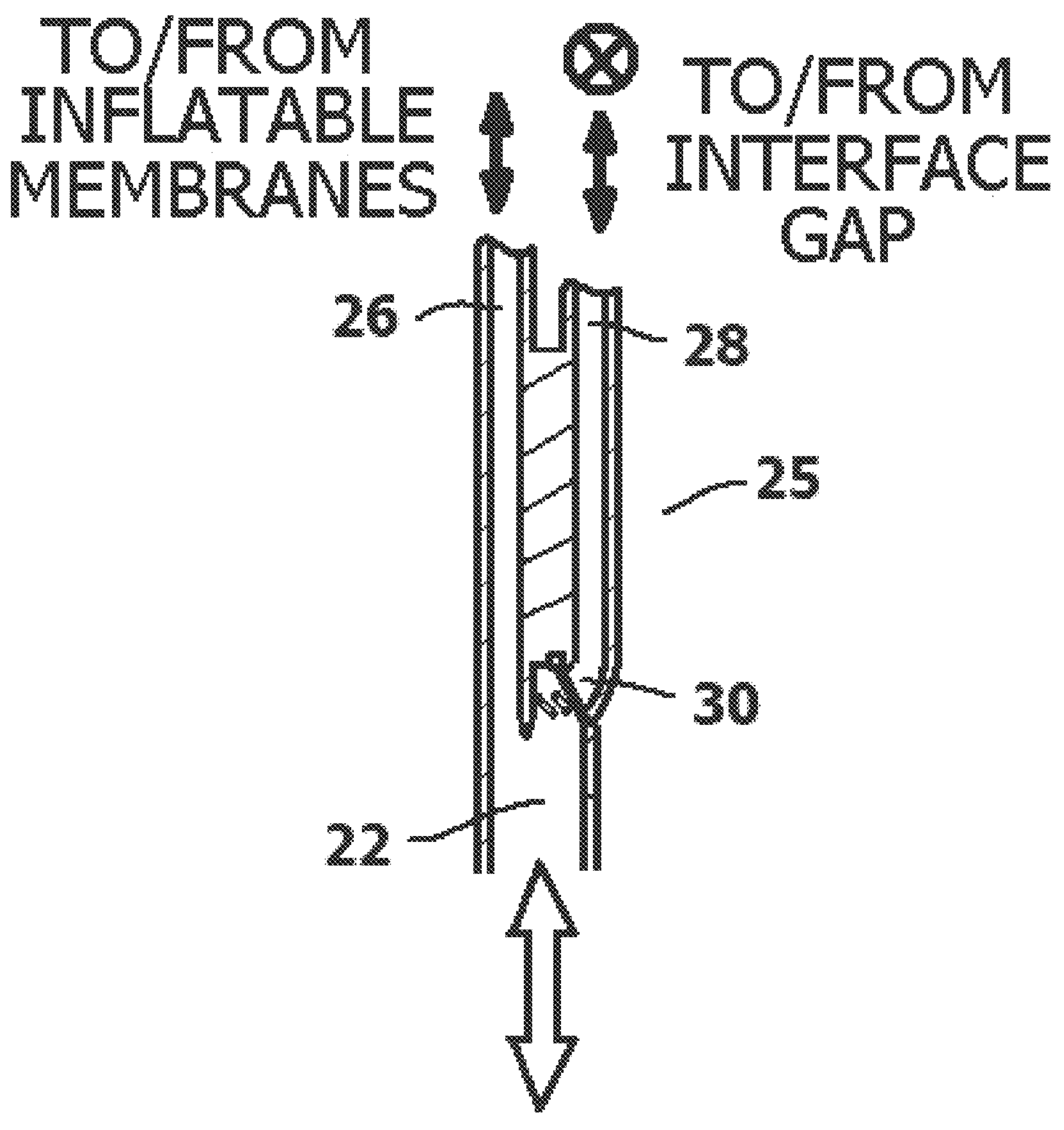
FIG. 4 is first embodiment of the valve assembly with one valve set into a closed condition.

Referring to FIG. 4 in conjunction with FIG. 3 and FIG. 2, it can be seen that in the valve assembly 25, the secondary tubes 26 interconnect to the primary tube 22. A pressure valve 30 is provided that separates the tertiary tube 28 from the primary tube 22, wherein the pressure valve 30 controls the flow of fluid between the tertiary tube 28 and the primary tube 22.

Figure 5:
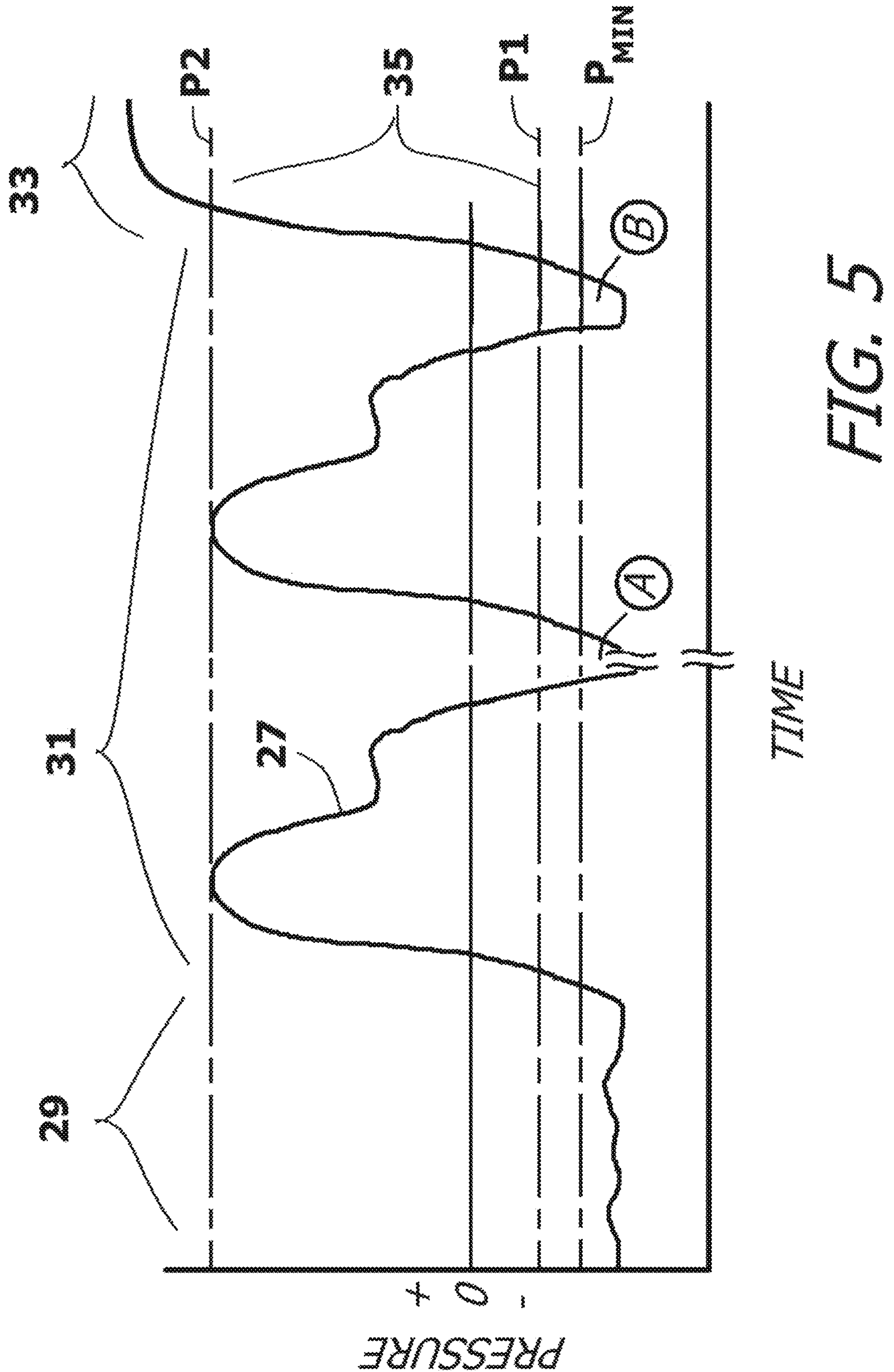
FIG. 5 is a graph that shows an exemplary pressure profile utilized by the cardiac assist system and the operational ranges of the valve assembly.

Referring to FIG. 5 in conjunction with FIG. 1, it will be understood that the fluid pump 24 generates a pressure profile 27 in accordance with programmed instructions. The pressure profile 27 produces different pressures in the primary tube 22 at different times. Furthermore, the pressure profile 27 produces different pressures during an installation window 29, and an operational period 31. During the installation window 29, the pressure profile 27 is designed to assist the cup assembly 12 in advancing through the body and passing onto the heart 11. During the operational period 31, the pressure profile 27 is used to both power the cup assembly 12 and keep the cup assembly 12 in position around the heart 11.

Figure 6:
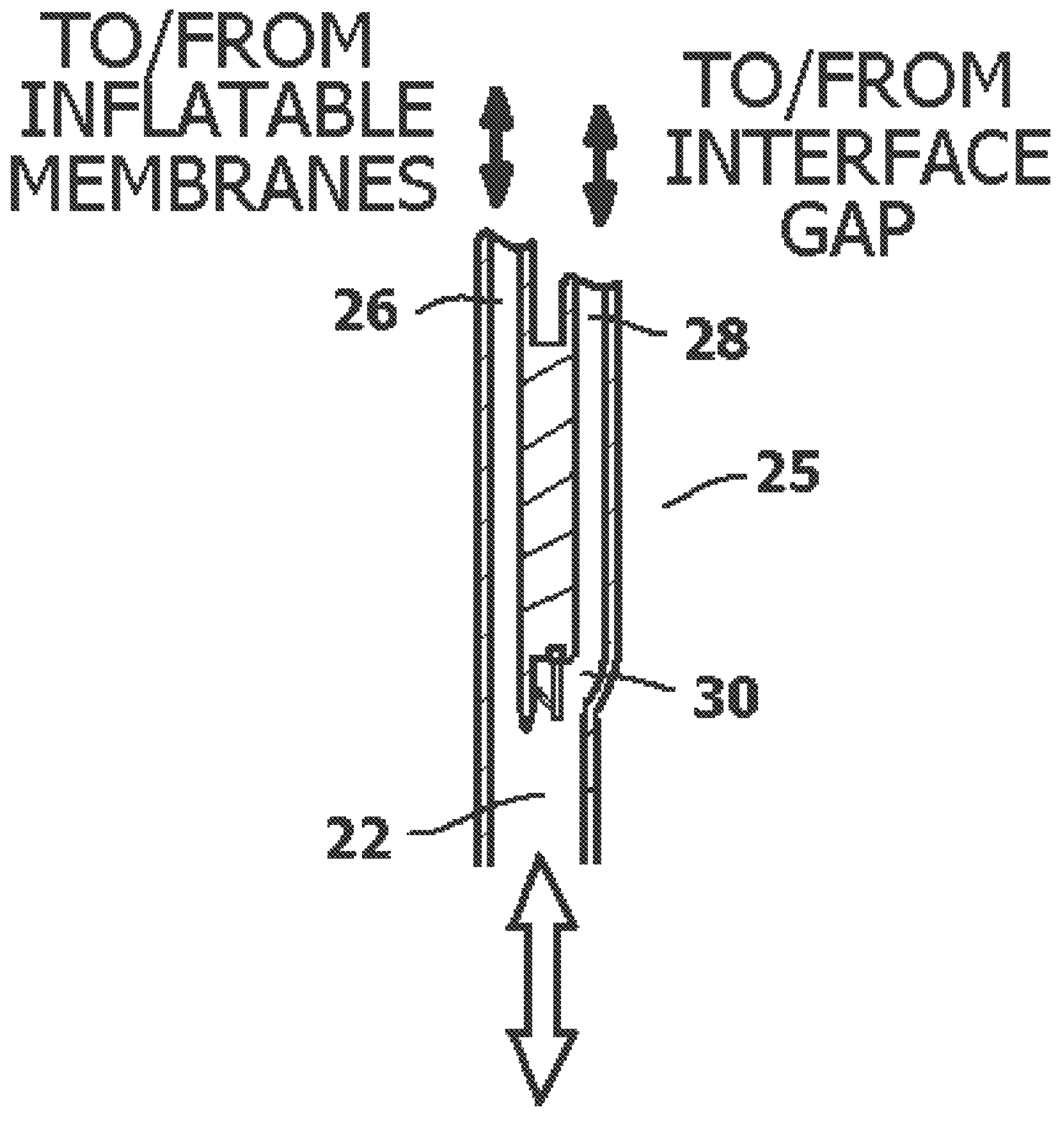
FIG. 6 shows the embodiment of the valve assembly used in FIG. 4 with the one valve set into an open condition.

Referring to FIG. 6, in conjunction with FIG. 5, it can be seen that the pressure valve 30 opens only when the fluid pressure in the pressure tube 22 falls below a threshold minimum pressure Pmin. See FIG. 6. Should the fluid pressure in the pressure tube 22 rise above the minimum pressure Pmin, the pressure valve 30 automatically closes and returns to the closed condition shown in FIG. 4.

In FIG. 5, in conjunction with FIG. 1 and FIG. 4, it can be seen that in the pressure profile 27 generated by the fluid pump 24, the pressure in the pressure tube 22 is below the threshold minimum pressure Pmin during the installation window 29. Accordingly, during the installation window 29, the pressure valve 30 is open and the receptacle 13 that is defined by the cup assembly 12 is exposed to the low pressure. This enables the cup assembly 12 to drain away any blood or other liquids tat may enter the receptacle 13. Furthermore, the low pressure in the receptacle 13 draws the cup assembly 12 onto the heart 11. The result is that during the installation window 29, the pressure tube 22 acts as a suction drain tube.

During the operational period 31, the pressure rises above the minimum pressure Pmin. This closes the pressure valve 30 and isolates the interface gap 20 between the heart 11 and the cup assembly 12. This condition is shown in FIG. 6. Due to the wet environment and the materials of the cup assembly 12, there is a degree of wet adhesion between the heart 11 and the cup assembly that preserves the low pressure condition and ensures the cup assembly 12 does not work free of the heart 11 when applying forces to the heart 11.

The threshold minimum pressure Pmin of the pressure valve 30 is set at a level so that the pressure profile 27 created by the fluid pump 24 periodically dips below the threshold minimum pressure Pmin during the operational period 31. In this manner, the low pressure condition in the interface gap space 20 can be actively maintained while the heart 11 is being actively assisted.

Figure 7:
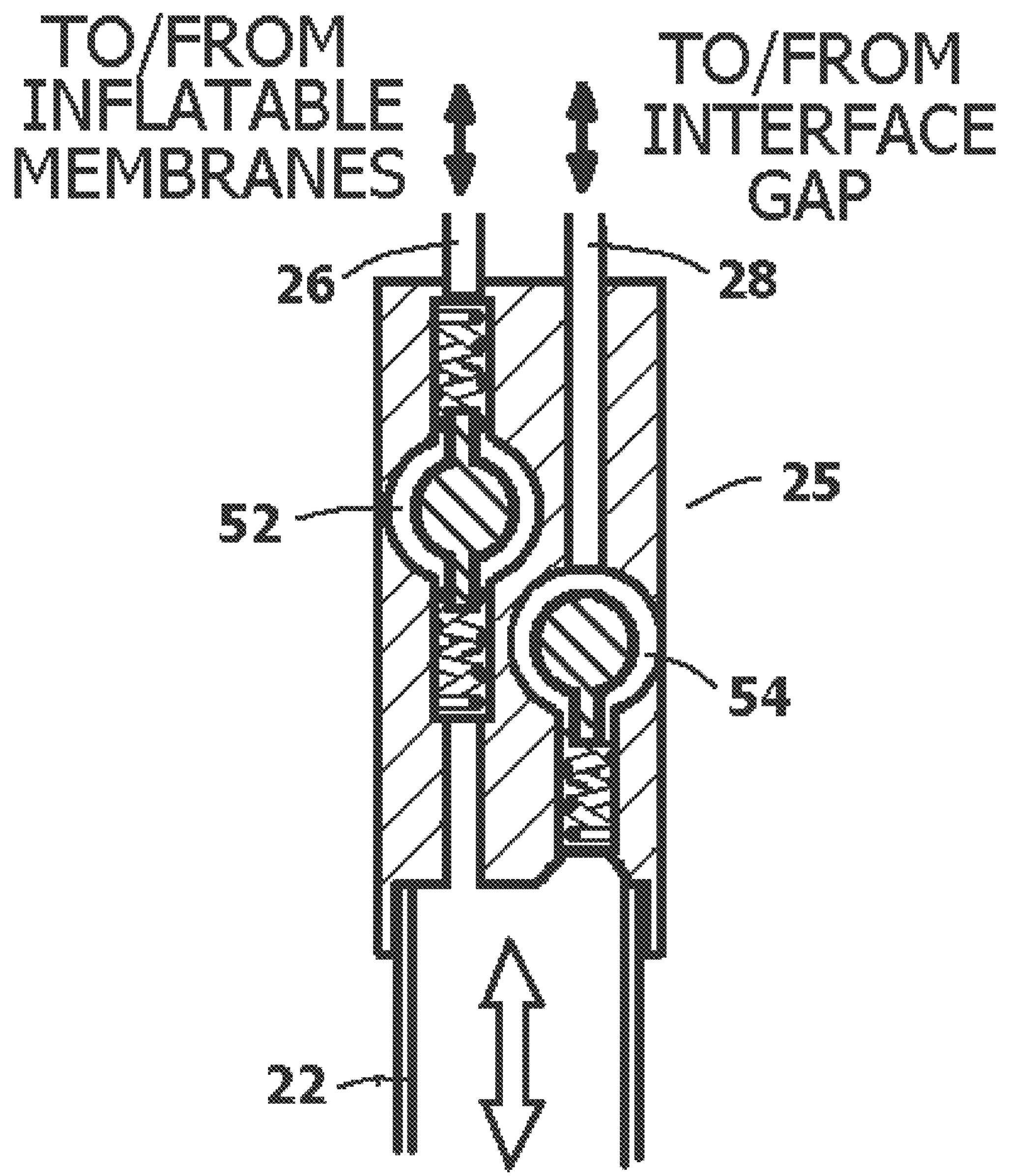
FIG. 7 is a schematic showing a second embodiment of the valve assembly containing a first valve and a second valve.

Referring to FIG. 7 in conjunction with FIG. 2, an alternate embodiment for a valve assembly 25 is shown. In this embodiment, the secondary tubes 26 are bundled together and terminate at a first valve 52. The first valve 52 is interposed between the secondary tubes 26 and the primary tube 22, wherein the first valve 52 controls the flow of fluid between the secondary tubes 26 and the primary tube 22. A second valve 54 is provided that is interposed between the tertiary tube 28 and the primary tube 22, wherein the second valve 54 controls the flow of fluid between the tertiary tube 28 and the primary tube 22. The first valve 52 is positioned a first distance from the apical endcap and the receptacle area it helps define. The second valve 54 is preferably positioned a second distance away from the apical endcap than is farther away than the first valve 52. The reason for the positional offset is later explained.

Referring to back to FIG. 5, it can be seen that the pressure profile 27 may include an extrication window 33 in addition to the installation window 29, and operational period 31. During the installation window 29, the pressure profile 27 is designed to assist the cup assembly 12 in advancing through the body and passing onto the heart 11. During the operational period 31, the pressure profile 27 both powered the cup assembly 12 and keeps the cup assembly 12 in position. Lastly, during the extrication window 33, the pressure profile 27 helps the cup assembly 12 separate from the heart 11.

Figure 8:
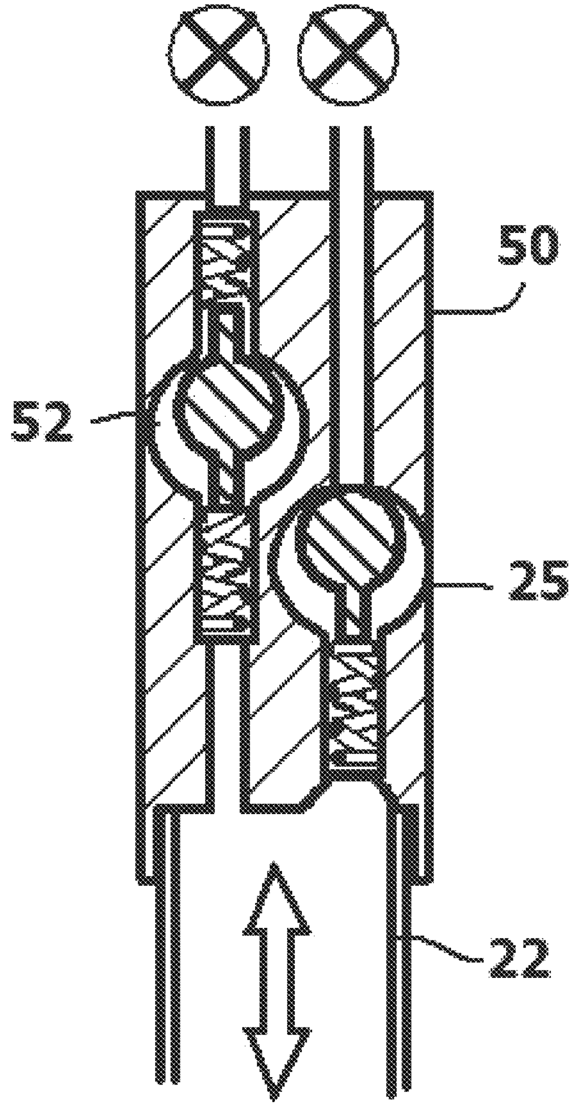
FIG. 8 shows the second embodiment of the valve assembly with both the first valve and the second valve closed due to a high pressure condition.
Figure 9:
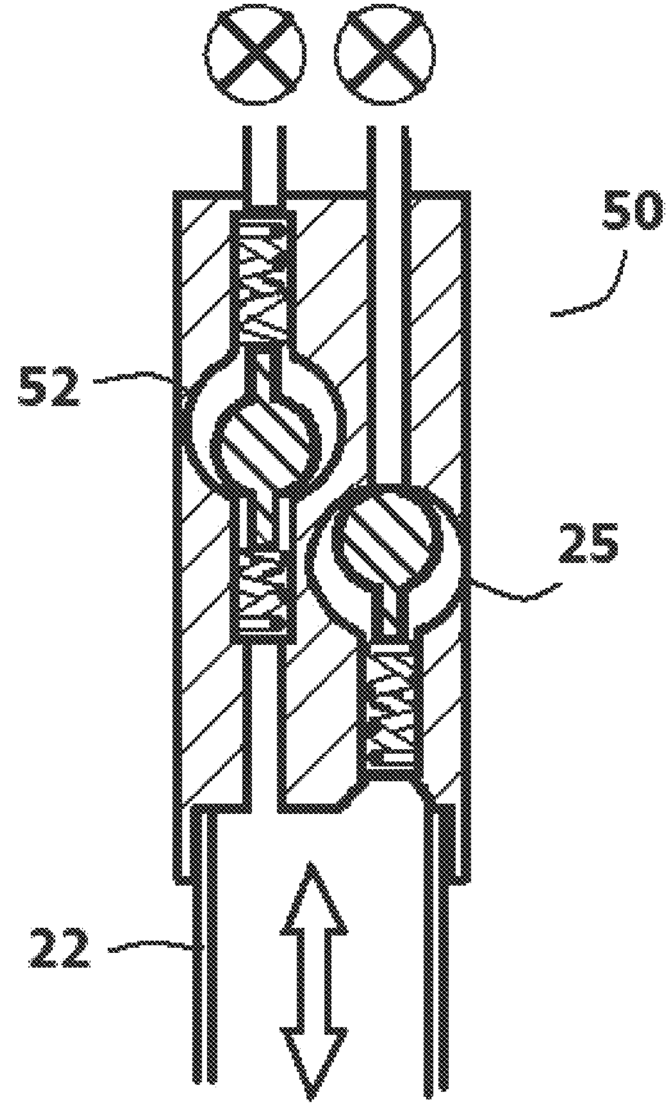
FIG. 9 shows the second embodiment of the valve assembly with the first valve open and the and the second valve closed.

Referring to FIG. 8, and FIG. 9 in conjunction with FIG. 5 and FIG. 2, it can be seen that the first valve 52 is a pressure range valve that stays open only when the fluid pressure flowing through the first valve 52 valve remains within a first valve operating range 35 that extends from a first pressure P1 to a second pressure P2. Should the fluid pressure surpass the second pressure P2, the first valve 52 closes. See FIG. 8. Conversely, should the fluid pressure fall below the first pressure P1, the first valve 52 also closes. See FIG. 9. The first valve 52 only remains open in the first valve operating range 35 at pressures between the first pressure P1 and the second pressure P2.

The second valve 54 is a standard pressure valve that stays open only when the fluid pressure flowing through the second valve 54 remains below the threshold minimum pressure Pmin. Should the fluid pressure rise above the threshold minimum pressure Pmin, the second valve 54 is closed, as shown in both FIG. 8 and FIG. 9.

Figure 10:
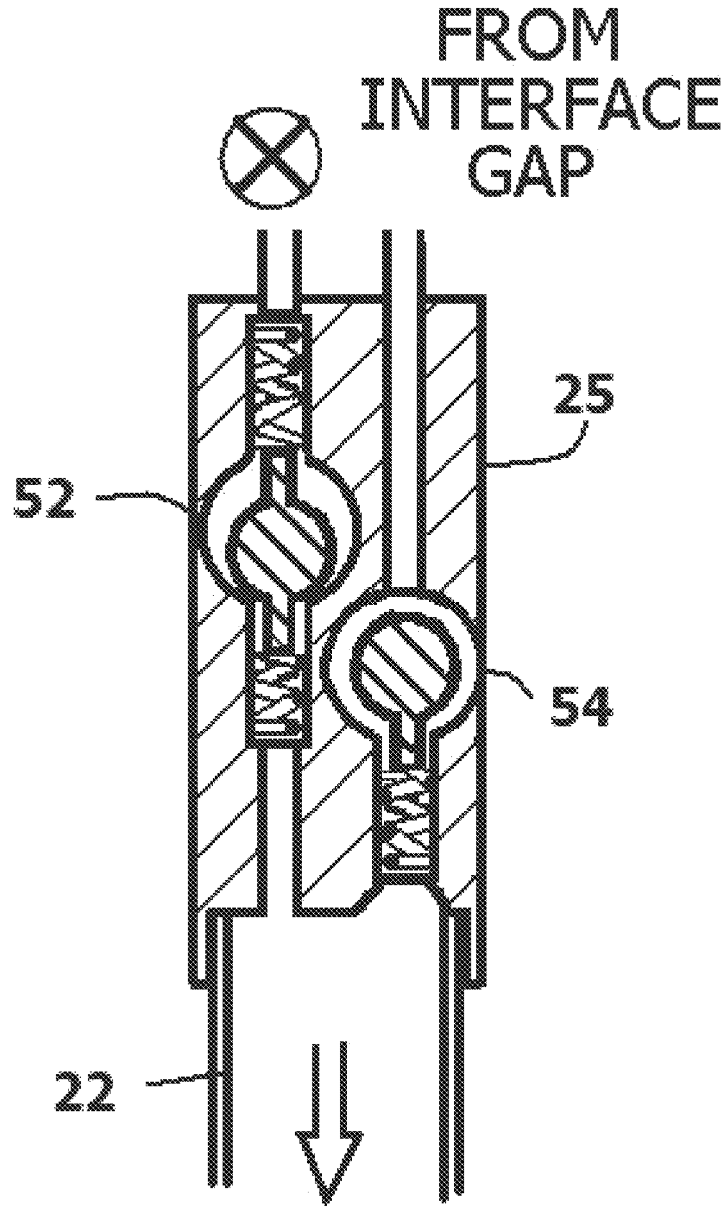
FIG. 10 shows the second embodiment of the valve assembly with the first valve closed and the and the second valve open.

The pressure profile 27 provided to the primary tube 22 varies with time. During the surgical insertion window 29, the cup assembly 12 is introduced around the heart 11. In this window, a low pressure is maintained in the cup assembly 12 to suction away fluids and to draw the cup assembly 12 onto the heart 11. Once in place on the heart 11, the pressure profile 40 varies from positive pressure to negative pressure to enable the cup assembly 12 to produce the diastolic and systolic assistance required by the heart 11. Referring to FIG. 10 in conjunction with FIG. 5 and FIG. 2, it can be seen that during the surgical insertion window 29, the pressure of the pressure profile 27 is below the threshold minimum pressure Pmin. The low pressure used during the surgical insertion window 42 is outside the operational pressure window of the first valve 52. Accordingly, the first valve 52 is closed. However, the low pressure during the surgical insertion window is in the open range of the second valve 54. Accordingly, the second valve 54 is open. Fluid can therefore be suctioned from the interface gap 20 while creating a negative pressure in the interface gap 20.

Referring back FIG. 9 in conjunction with FIG. 5 and FIG. 2, it can be seen that once the cup assembly 12 is in place over the heart 11, the inflatable membranes 16 are selectively inflated using the pressure profile 27. As a positive pressure is created in the primary tube 22, the pressure raises above the threshold minimum pressure Pmin of the second valve 54. Accordingly, the second valve 54 closes and fluid is prevented from flowing into the interface gap 20. In this manner, the negative pressure in the interface gap 20 is maintained. As the fluid pressure continues to increase, the operating range 35 of the first valve 52 is reached and the first valve 42 opens. This enables the inflatable membranes 16 to be freely inflated and deflated within the limits of the operational range 35, without effecting the negative pressure in the interface gap 20. Periodically, the fluid pressure in the primary tube 22 is momentarily dropped below the operational range of the first valve 52 and into the open range of the second valve 54. This is shown as point A and point B on the graph of FIG. 5. This closes the first valve 52 and opens the second valve 54 as is shown in FIG. 10. This enables air and fluids to be periodically suctioned out of the interface gap 20 to maintain the negative pressure in the interface gap 20.

Figure 11:
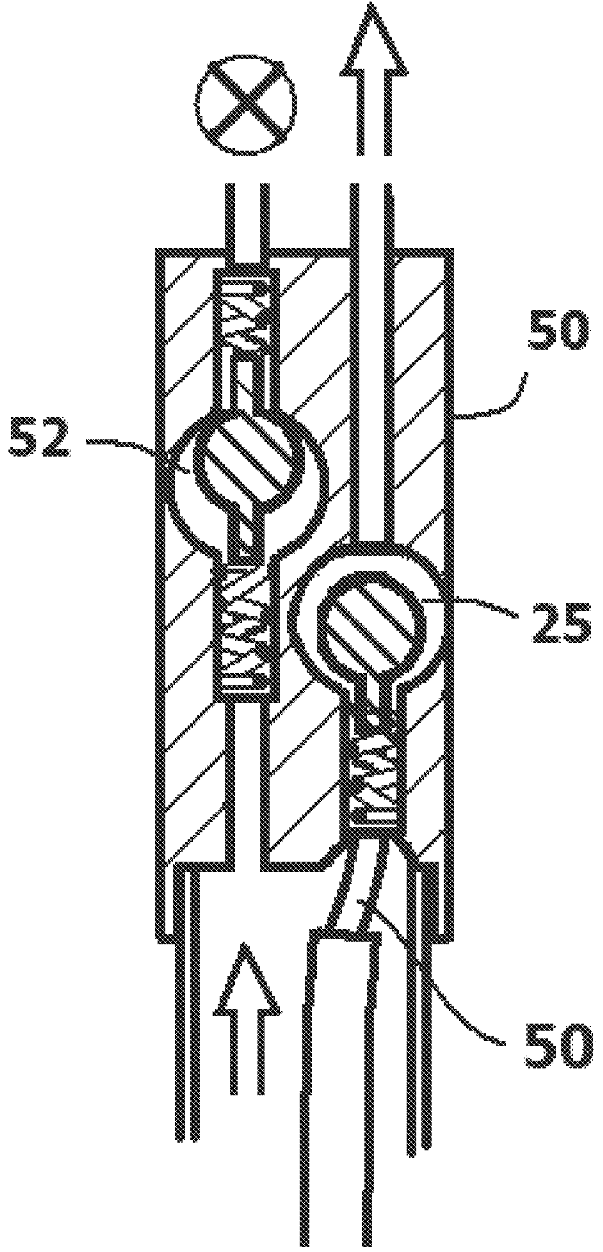
FIG. 11 shows the second embodiment of the valve assembly engaged by a catheter to open the second valve.

Referring to FIG. 11 in conjunction with FIG. 5 and FIG. 2, it can be seen that to remove the cup assembly 12, a catheter 60 is advanced into the primary tube 22. The catheter 60 passes into the second valve 54 since the second valve 54 is located farther from the cup assembly 12 than is the first valve 52. As the catheter 60 enters the second valve 54, the presence of the catheter 60 disables the second valve 54 and holds the second valve 54 open. A pressure higher than the operational range of the first valve 52 is then provided. This closes the first valve 52 and prevents over inflation of the inflatable membranes 16. Simultaneously, the pressure increases in the interface gap 20 between the heart 11 and the cup assembly 12. The increased pressure acts to separate the cup assembly 12 from the heart 11 as the cup assembly 12 is removed from the body.

It will be understood that by using one primary tube 22 to transfer fluid forces to the cup assembly 12, the cup assembly 12 can be installed, operated indefinitely, and removed.

Figure 12:
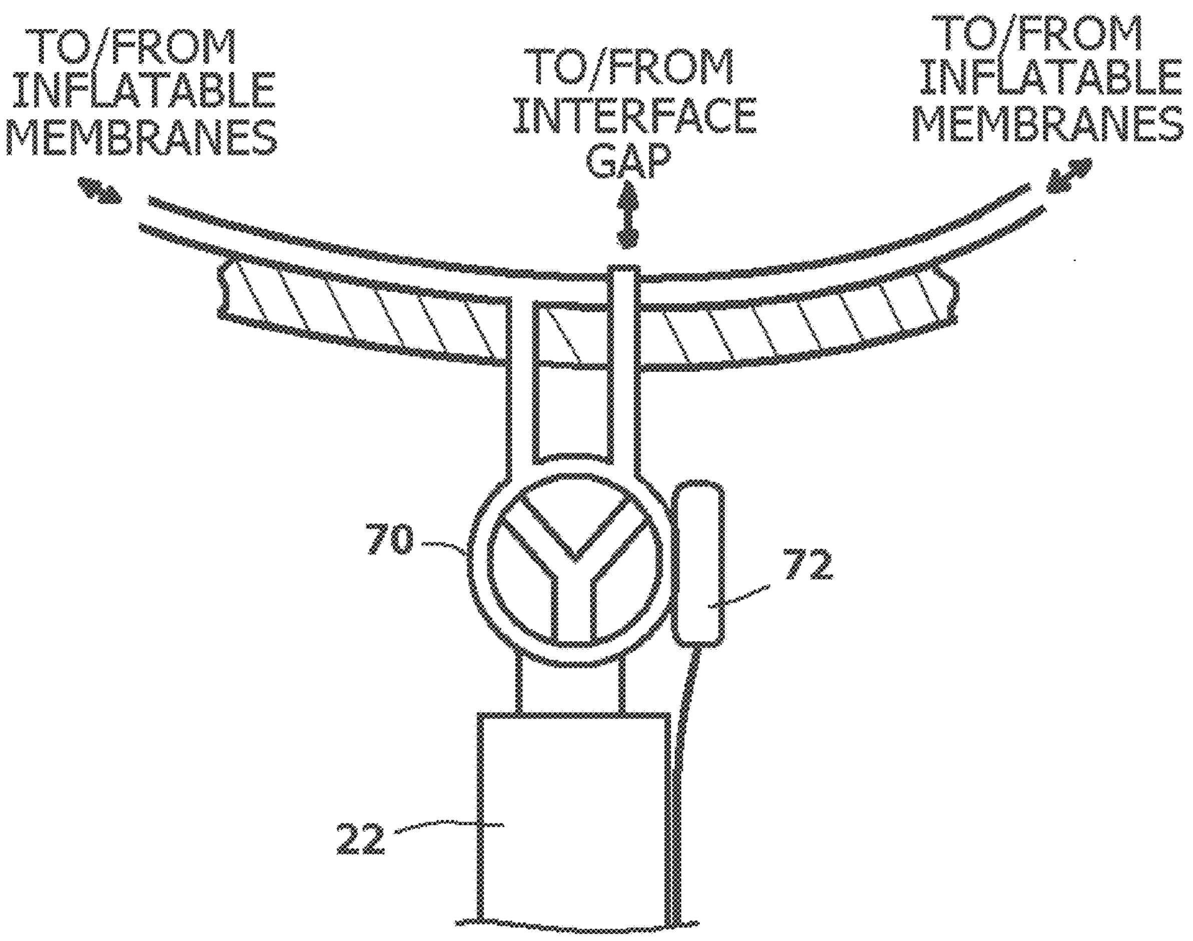
FIG. 12 is a schematic showing a third embodiment for the valve assembly.

Referring to FIG. 12, an alternate embodiment of the present invention is shown that utilizes an electrically operated 3-way valve 70. The 3-way valve 70 connects to the primary tube 22 and can direct fluid pressure to either the inflatable membranes 16 or the interface gap 20. The 3-way valve 70 is electronically operated using wires 72 that are attached to either the interior or exterior of the primary tube 22. By selectively operating the split valve 70 and the fluid pressure in the primary tube 22, the inflatable membranes 16 can be selectively pressurized while maintaining suction in the interface gap 20.

In all the previous embodiments, one valve assembly is provided that connects the tubes of the inflatable membranes to the primary tube. However, certain heart pump assemblies have a modular structure and are assembled in vivo. In such a construct, it may be easier to provide each modular element with its own valve assembly as opposed to connecting the modular elements to one valve assembly in the body.

Figure 13:
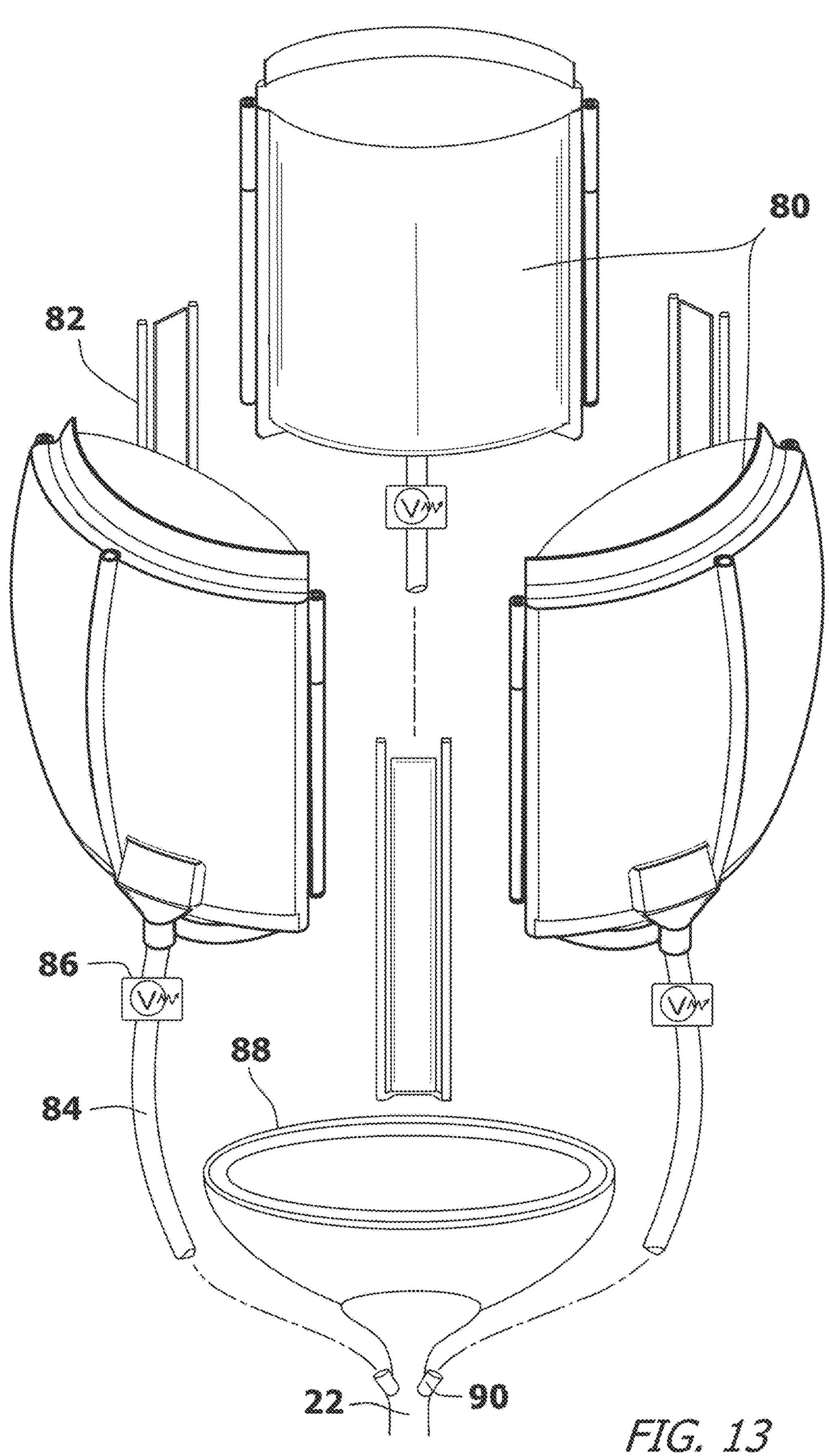
FIG. 13 shows a modular heart pump with a fourth embodiment of a valve assembly.

Referring to FIG. 13, an embodiment of the present invention is shown that has modular panels 80 that interconnect in the body to form a heart pump. The modular panels 80 can be deployed one at a time and are interconnected using panel connectors 82. Each of the modular panels 80 has its own fluid tube 84 and a valve assembly 86 that controls fluid flow through the fluid tube 84. The valve assembly 86 has the same function as has been explained in the prior embodiments.

The modular panels 80 are set upon an apical base 88. The primary tube 22 extends into the apical base 88. Tube connectors 90 are provided on the primary tube 22 so that the fluid tubes 84 from the modular panels 80 can be connected to the primary tube 22 in the body.

It will be understood that the embodiments of the present invention that are illustrated and described are merely exemplary and that a person skilled in the art can make many variations to those embodiments. All such embodiments are intended to be included within the scope of the present invention as defined by the claims.

What is claimed is:

1. A method, comprising:

providing a fluid powered heart pump that defines a receptacle area having at least one inflatable membrane that selectively expands into said receptacle area when inflated with a fluid, providing a first tube for passing the fluid into and out of said at least one inflatable membrane;

providing a second tube for passing said fluid into and out of said receptacle area;

providing a single pressure tube for supplying said fluid to said first tube and said second tube;

providing a valve assembly affixed to said heart pump, wherein said valve assembly is disposed between said single pressure tube and both said first tube and said second tube;

placing said heart pump and said valve assembly in vivo wherein said receptacle area receives at least a portion of a heart therein;

creating fluid flow with a controlled pressure profile with a fluid pump;

directing said fluid flow to said valve assembly through said single pressure tube, wherein said valve assembly selectively controls flow of said fluid between said single pressure tube and both said first tube and said second tube.

2. The method according to claim 1, further including opening fluid flow between said heart pump and said single pressure tube only in a first pressure range between a preselected maximum pressure and a preselected minimum pressure.

3. The method according to claim 2, further including opening fluid flow between said receptacle area and said single pressure tube only in a second pressure range that is below said preselected minimum pressure of said first pressure range.

4. The method according to claim 1, further including mechanically controlling said valve assembly by advancing a catheter into said valve assembly through said single pressure tube.

5. The method according to claim 1, wherein providing the fluid powered heart pump includes providing a cup assembly that defines said receptacle area, wherein said cup assembly contains said at least one inflatable membrane.

6. The method according to claim 5, wherein said valve assembly includes a first valve that enables fluid flow between said at least one inflatable membrane and said single pressure tube only within a first pressure range.

7. The method according to claim 6, wherein said valve assembly includes a second valve that opens only when pressure in said single pressure tube falls below a minimum pressure value outside of said first pressure range.

8. The method according to claim 7, wherein said first valve is a first distance from said cup assembly and said second valve is a second distance from said cup assembly that is farther than said first distance.

9. The method according to claim 7, wherein said first valve is open in said first pressure range.

10. The method according to claim 7, wherein said second valve can be mechanically opened by advancing a catheter into said second valve through said single pressure tube.

11. The method according to claim 1, wherein said valve assembly is electrically operated using a wire that is affixed to said single pressure tube.

* * * * *